(12) United States Patent
Nortmann et al.

(10) Patent No.: US 9,443,057 B2
(45) Date of Patent: Sep. 13, 2016

(54) METHOD AND SYSTEM FOR IMAGE ACQUISITION WORKFLOW

(75) Inventors: Charles Nortmann, Richmond Heights, OH (US); Julianne Murray Suhy, Broadview Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 67 days.

(21) Appl. No.: 14/114,554

(22) PCT Filed: Apr. 3, 2012

(86) PCT No.: PCT/IB2012/051626
§ 371 (c)(1),
(2), (4) Date: Oct. 29, 2013

(87) PCT Pub. No.: WO2012/150514
PCT Pub. Date: Nov. 8, 2012

(65) Prior Publication Data
US 2014/0064592 A1 Mar. 6, 2014

Related U.S. Application Data

(60) Provisional application No. 61/481,945, filed on May 3, 2011.

(51) Int. Cl.
*G06K 9/00* (2006.01)
*G06F 19/00* (2011.01)

(52) U.S. Cl.
CPC .................................. *G06F 19/321* (2013.01)

(58) Field of Classification Search
CPC .................. G06F 19/321; G06T 2207/30004; G06Q 50/24
See application file for complete search history.

(56) References Cited

U.S. PATENT DOCUMENTS

| 5,241,472 A | 8/1993 | Gur et al. |
| 5,432,871 A | 7/1995 | Novik |
| 6,241,668 B1 | 6/2001 | Herzog |
| 6,891,920 B1 * | 5/2005 | Minyard ............... A61B 6/469 378/37 |
| 7,152,785 B2 | 12/2006 | Metz et al. |
| 7,573,034 B2 | 8/2009 | Heath et al. |
| 7,703,020 B2 | 4/2010 | Bhattaru |
| 8,483,456 B2 * | 7/2013 | Nagatsuka ............... A61B 5/08 382/128 |
| 2002/0023172 A1 * | 2/2002 | Gendron et al. ............. 709/238 |
| 2004/0001154 A1 * | 1/2004 | Obrador ..................... 348/231.2 |
| 2005/0267351 A1 * | 12/2005 | Humphrey ........... G06F 19/321 600/408 |
| 2009/0059772 A1 * | 3/2009 | Samari ..................... 369/124.07 |
| 2010/0185459 A1 | 7/2010 | Vera et al. |

FOREIGN PATENT DOCUMENTS

| EP | 1868124 A2 | 12/2007 |
| WO | 2011064695 A2 | 6/2011 |

* cited by examiner

*Primary Examiner* — Amara Abdi

(57) ABSTRACT

A method and system for image acquisition workflow are provided. The imaging acquisition system is configured to implement an imaging acquisition protocol. Then imaging data is acquired according to the protocol. At least some identification information is entered during the imaging data acquisition. The entered identification information may be checked for errors during the imaging acquisition. The imaging data and identification information are then stored together. Identification information may include, for example, a patient's name and/or identification number, date of birth, sex, height, weight, race or ethnicity, and perhaps yet other information.

19 Claims, 4 Drawing Sheets

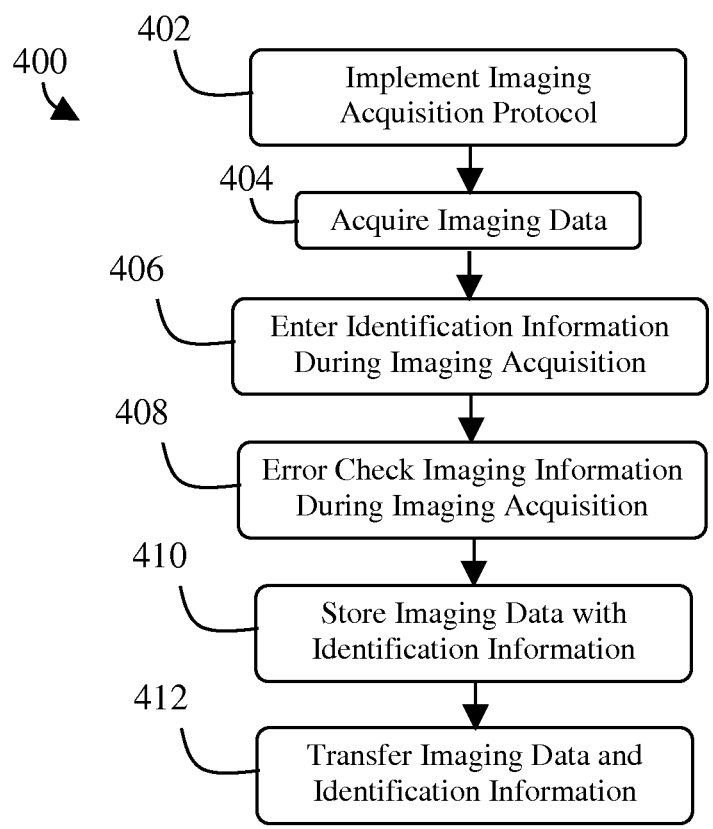

METHOD AND SYSTEM FOR IMAGE ACQUISITION WORKFLOW

CROSS REFERENCE TO RELATED APPLICATIONS

This application is a national filing of PCT application Serial No. PCT/IB2012/051626, filed Apr. 3, 2012, published as WO 2012/150514 A1 on Nov. 8, 2012, which claims the benefit of U.S. provisional application Ser. No. 61/481,945 filed May 3, 2011, which is incorporated herein by reference.

The present application relates generally to the imaging arts and more particularly to a method and system for image acquisition workflow. The application subject matter finds particular use in connection with medical imaging systems such as for example general radiography (GR), x-ray computed tomography (CT), magnetic resonance imaging (MR), nuclear medicine (NM), and combinations thereof. Nuclear medicine includes, for example, single photon emission computed tomography (SPECT) imaging systems and positron emission tomography (PET) imaging systems.

However, in its broader aspects, the application subject matter is not limited to the medical imaging field, and may apply in non-medical fields. These imaging systems typically gather imaging data regarding an object, such as a human person, and record that imaging data for later analysis and use. Such uses include for example medical diagnosis, tracking the growth or properties of a tumor within a person's body, looking for illegal or dangerous items such as guns and knives for security purposes, and the like. Thus, while one embodiment is medical imaging and much of the following description relates to the medical imaging field, the present invention applies in other fields as well.

In most image reconstruction, processing, analysis, and visualization applications, images are generated and recorded for a specific reason or reasons. Often these images are made in connection with an investigation, such as determining whether a patient has cancer, or determining the extent of a cancer, or determining whether a bone has been broken, or determining whether an organ is functioning properly. Therefore it is important to record certain identification information when recording the imaging data. Identification information includes, for example, a patient's name and/or identification number and a patient's date of birth. The identification information often further identifies the facility where the image was taken, as well as the technologist who controlled the imaging equipment to acquire the imaging data, and perhaps other information.

The field of medical imaging has evolved from the early days of radiography. In traditional radiography, latent images were captured on film and then chemically processed to produce a visible analog image such as a photograph. These analog images were typically identified by a mechanism to incorporate pertinent identification information directly on the film which also contained the recorded image. The order and mechanism of image collection and identification often forced the technologist to enter the identification information prior to recording the image. It was often difficult to correct errors in the identification information which were recorded on the analog film along with the image. Thus, the recording of patient identification information was typically not adjustable after the imaging acquisition began.

In more modern medical imaging, the images are initially acquired, stored and archived in a digital format which can be displayed on a computer screen. Digital imaging involves the storing, transferring and archiving of the image in an electronic form on a computer-readable medium. Common digital imaging file formats include .pdf, .jpg, .gif, and many other file formats. Conceptually, such medical digital image files are composed of two portions. A first portion contains the imaging data itself. A second portion contains identification information for the imaging data of the first portion. Such identification information can take various forms and content. It typically at least identifies the subject being imaged, such as for example by name and/or identification number. It often also includes basic information about the imaged subject, such as for example date of birth or age, sex, height, weight, race or ethnicity, personal medical history, family medical history, and the like. Additional identification information related to the image data may also be recorded, such as for example the date and time the imaging data was recorded, the matrix size and bit depth of the data, the technologist who operated the equipment, and the like.

Traditionally, following the standard practice from analog image gathering, the identification information has been entered prior to recording digital images. Requiring patient information and complete setup prior to image acquisition is, however, inefficient. In many modalities, image acquisition occurs over several minutes. The total time required for an examination would be reduced if this serial process were not required. Moreover, manual entry of the patient identification information presents an opportunity for entry errors. Without an opportunity to correct entered information, incorrectly identified images may be stored in the archive.

Standards have been developed to facilitate recording, associating and transferring medical digital imaging data with identification information. One common standard is the Digital Imaging and Communication in Medicine (DICOM) standard. The DICOM standard defines a large number of parameters that may be included in the identification information portion, which is called the "header." Using a best practice, the header information should be complete when the imaging data is initially transferred from the imaging acquisition system for storage and archiving at another location, in order to reduce the likelihood of a data entry error or loss of the imaging data.

According to one aspect of the present invention, a method and system for an image acquisition workflow are provided. Identification information is entered while acquired imaging data is being collected. This optimizes the workflow by reducing the time needed for the overall image identification and recordation process, and also offers an opportunity to correct entry errors prior to archiving the image.

In the workflow, the imaging acquisition system is configured to implement an imaging acquisition protocol. The protocol may be pre-defined or manually entered by the technologist. The technologist prepares for the acquisition by properly positioning the patient in the imaging system. Then imaging data is acquired according to the protocol. At least some identification information is entered during the imaging data acquisition. The operator may either enter the patient information manually or select patient information from a management system, such as a radiology information system (RIS) or hospital information system (HIS) used for scheduling. The entered identification information may be checked for errors during the imaging acquisition, without the time pressure of needing to begin the acquisition quickly to avoid delaying the completion of the examination. The imaging data and identification information are then stored together. They may be transferred together to a physically remote location for archiving or other purposes. Even if some or all of the identification information is entered prior to acquisition, the ability to adjust the identification information during the acquisition gives the opportunity to correct entry errors prior to sending images to the archive. This is a new insight into digital image acquisition, given that the current model is based upon the assumptions that are inherent in an analog film-based approach.

Items such as the patient's name, identification number, date of birth, and height and weight may be entered as identification information. In addition, clinical information related to the examination may be needed, and may be entered manually or selected from a records management system, such as a pharmacy or radiopharmacy system. Such items as the administered radiopharmaceutical activity or iodinated contrast volume may be entered as part of the identification information.

Numerous advantages and benefits will become apparent to those of ordinary skill in the art upon reading the following detailed description of several embodiments. The invention may take form in various components and arrangements of components, and in various process operations and arrangements of process operations. The drawings are only for the purpose of illustrating many embodiments and are not to be construed as limiting the invention.

FIG. 4 is an illustration of an exemplary method for an image acquisition workflow.

Figure 1:
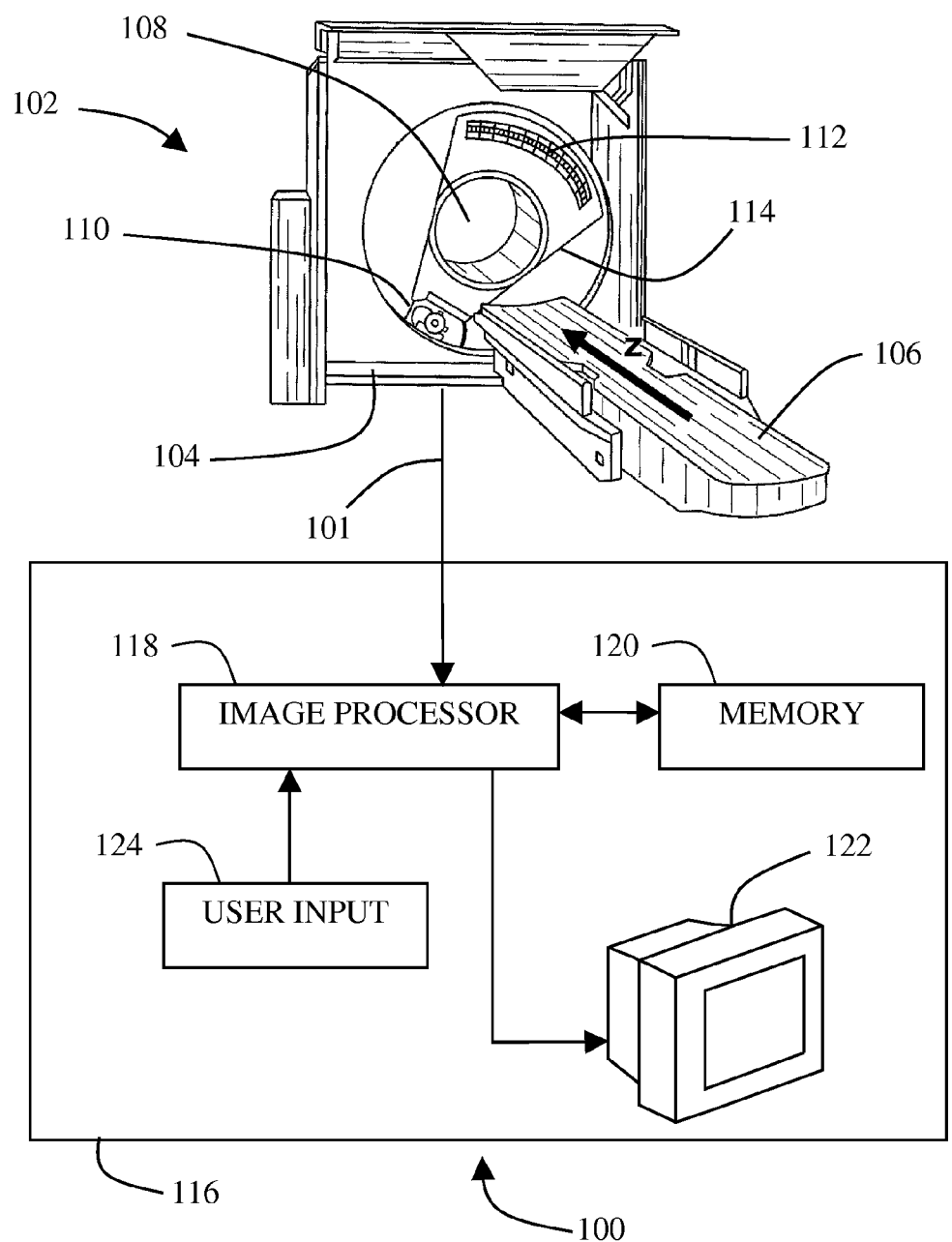
FIG. 1 is an exemplary medical CT imaging system, with a portion of the stationary gantry cut away to reveal the rotating x-ray source and data measurement system within the gantry.

The subject matter of the present disclosure finds use in connection with any imaging system, for example, a CT imaging system. More specifically, with reference to FIG. 1, in one embodiment the imaging system 100 is a medical CT imaging system. A CT imaging acquisition system 102 includes a gantry 104 and an object support 106 such as a table or couch which moves along the z-axis. A patient or other object to be imaged (not shown) lies or is placed down on the object support 106 and is moved to be disposed within an aperture 108 in the gantry 104. Once the patient or object is in position within the aperture 108, an x-ray source 110 emits a projection of x-rays to be gathered by an x-ray data measurement system 112 inside the gantry 104. (A portion 114 of the gantry 104 is cut away in FIG. 1 to show the x-ray source 110 and x-ray data measurement system 112 which are housed inside the gantry 104.) The x-ray source 110 and data measurement system 112 rotate together around the aperture 108 to acquire and record CT imaging data from various positions. In some embodiments such rotation may occur while the object support 106 is stationary. In other embodiments such rotation may occur in conjunction with linear movement of the object support 106 along the z-axis in a "helical" scan. The rotation is possible because the x-ray source 110 and the data measurement system 112 are each mounted to a common rotor (not shown) inside the gantry 104.

The data measurement system 112 of the CT imaging acquisition system 102 thus acquires CT imaging data in the form of detected x-rays. The system 102 then transfers the acquired CT imaging data on to a CT imaging, processing and display system 116 through a communication link 101. Although the systems 102 and 116 are shown and described here as being separate systems for purposes of illustration, they may in other embodiments be part of a single system.

When the systems 102 and 116 are separate systems, the communication link 101 may be any link which permits the transfer of data between the systems, such as a Local Area Network, the Internet, a physical transfer of a memory storage medium such as a computer diskette, CD-ROM, or flash drive, or the like. The communication link 101 may be wired, wireless, or a combination thereof. Thus, the systems 102 and 116 may be located in different rooms, different buildings, or even different cities. Most typically, however, the systems 102 and 116 are either in the same room or in separate but adjoining and connected rooms. An operator may then use the system 116 to control the system 102 during the imaging acquisition process.

Via the communication link 101, the acquired CT imaging data passes to an image processor 118 which stores the acquired CT imaging data in a memory 120. The image processor 118 may apply well-known image reconstruction techniques to electronically process the acquired CT imaging data and generate reconstructed imaging data, comprising digital images of the imaged patient or other object. The image processor 118 can show the resulting reconstructed imaging data on an associated display 122. A user input 124 such as a keyboard and/or mouse device may be provided for a user to control the processor 118.

The imaging system 100 may be a stand-alone unit which provides only CT-based imaging, as is shown in FIG. 1. Although not shown here, the imaging system 100 may additionally include appropriate components for PET and/or SPECT imaging, or some other imaging modality, in conjunction with the CT-based imaging components. Also, although the exemplary system of FIG. 1 is a CT imaging system, the present method also applies to many other imaging systems such as PET systems, SPECT systems, MRI systems, and combinations thereof. All such systems have an imaging acquisition component (such as the CT system 102) and an imaging processing component (such as the CT system 116). The imaging acquisition component generates, measures and records one or more different kinds of acquired imaging data concerning an imaged subject. The imaging processing component receives the acquired imaging data and in some cases processes it to generate reconstructed imaging data which can be viewed on a display. In other cases, such post-acquisition processing may not be necessary in order to display the imaging data for review by users, or it might be performed at a later time by a different system.

In many instances, it is desirable for the imaging data to be transferred to yet other computer systems for review, consideration and perhaps manipulation by many different users. These users may be located in many different locations, and may use many different kinds of computer systems to view the imaging data. For example, in the particular context of medical imaging data, several medical professionals with differing kinds of expertise may need to see the imaging data in order for the patient to make medical decisions in consultation with a primary care physician. The transfer of imaging data may be accomplished through any type of communication link, such as the examples discussed above in connection with the communication link 101.

Thus the functions described herein can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory such as memory 120, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic shown and described herein preferably resides in or on a computer readable medium such as the memory 120. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

Figure 2:
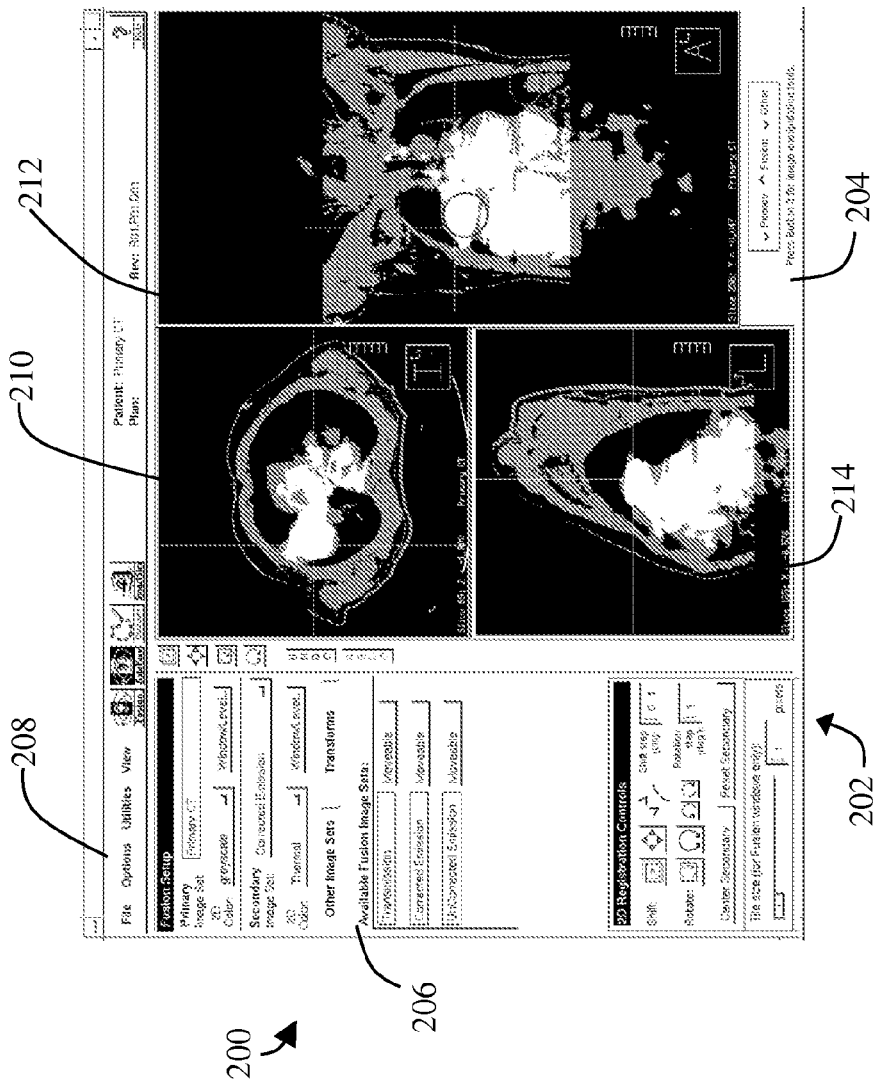
FIG. 2 shows an image display tool.

The present disclosure provides a method and system for an image acquisition workflow. An exemplary embodiment of a digital imaging display 200 is illustrated in FIG. 2. As shown there, an image display tool 202 includes an image display portion 204, an image control panel portion 206, and a menu portion 208.

The image display portion 204 contains the three standard medical image views of reconstructed imaging data: a transverse plane view 210, a coronal plane view 212, and a sagittal plane view 214. One horizontal line and one vertical line in each of the three views 210, 212 and 214 illustrate the respective orientations of the three views; the intersection point of the lines in each view is the only point common to all three views.

The image control panel portion 206 contains various options for the user to display imaging data in the image display portion 204. A user may use the control panel portion 206 to choose what imaging data to display (e.g. CT, PET, or both), the location of the three imaging planes 210, 212 and 214 within the displayed reconstructed imaging data, whether to use color or grayscale, and the like.

The menu portion 208 contains other options for the user to manipulate the imaging data displayed in the image display portion 204. Thus, a user may use the menu portion 208 to upload an identified acquired or reconstructed set of imaging data, or to copy selected images for export, and the like.

Figure 3:
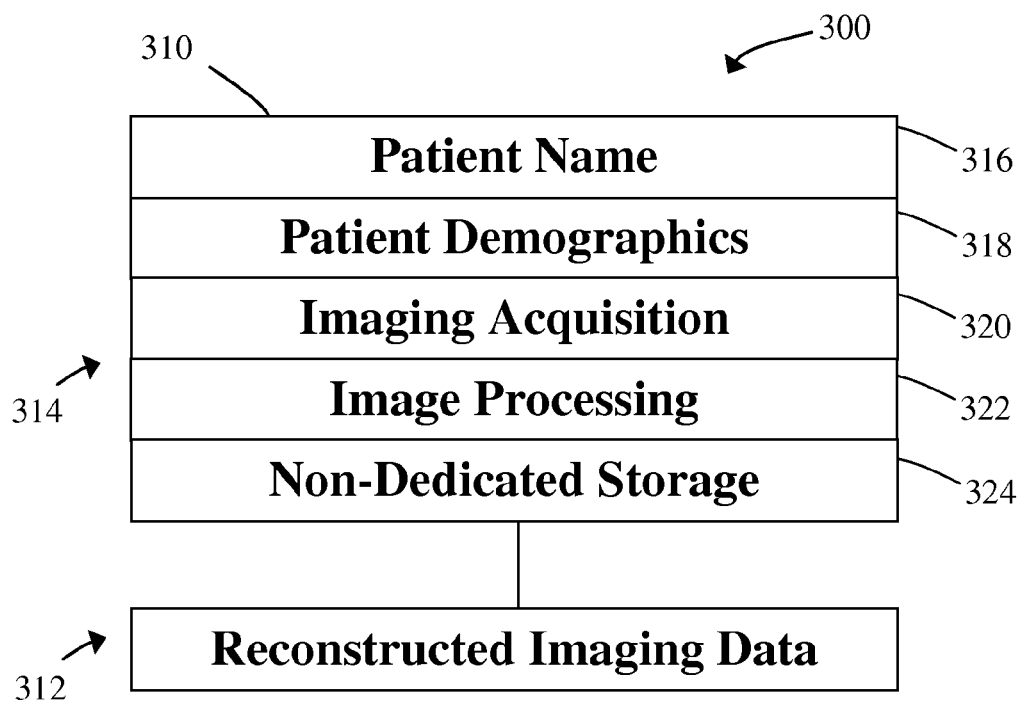
FIG. 3 is a schematic illustration of a conventional DICOM image file format.

In one particular embodiment, the present invention is used in conjunction with the Digital Imaging and Communications in Medicine ("DICOM") standard. The DICOM standard aims to facilitate the storage, distribution and viewing of reconstructed medical images such as CT images, PET images, SPECT images, MRI images, and the like. DICOM is the most common standard for storing, transmitting and receiving medical imaging data in use today. The DICOM standard defines an imaging file format. FIG. 3 is a schematic illustration of the conventional DICOM file format 300. Pursuant to the DICOM image file format 300, a single DICOM file 310 contains an imaging data portion 312 and a header portion 314. The imaging data portion 312 stores the imaging data, i.e., the two-dimensional or three-dimensional matrix of intensity or other values which define a pixilated or voxelated image. This data 312 corresponds for example to the three views 210, 212 and 214 of a digital imaging display 200. The header portion 314 stores information related to the imaging data portion 312. Other file formats use a similar header/image data format.

The information stored in the header portion 314 includes identification information. The identification information might include, for example, the name of the patient 316 being imaged. The identification information in the header portion 314 also might include demographic information 318 concerning the patient, such as for example birth date, height, weight, sex, and the like. The identification information also might include image acquisition information 320 concerning the imaging data 312, such as for example the type of imaging scan performed (CT, PET, etc.), the duration of the imaging acquisition, the current applied to the x-ray tube for a transmission x-ray imaging acquisition, the type of radiopharmaceutical used for an emission imaging acquisition, the pixel or voxel matrix size of the reconstructed imaging data, and the like. The identification information also might include image processing information 322, concerning how the acquired imaging data was processed to generate reconstructed imaging data stored in portion 312. Under the DICOM standard, the header portion 314 also includes a portion of non-dedicated or free memory 324 which may be used by a particular user to store any information defined by that user. In that way, the DICOM standard permits some limited user customization to the types of identification information stored in the header portion 314.

Typically, one or more technologists operate the imaging system to generate the acquired imaging data, and also perhaps to process the acquired imaging data to generate reconstructed imaging data. These technologists are qualified by their education, training and experience to operate the imaging system and manipulate the imaging data. Thus a method for an image acquisition workflow is provided. An exemplary such method 400 is illustrated in FIG. 4. The method 400 starts with the technologist implementing an imaging acquisition protocol 402. The protocol 402 most often will follow a prescription which has already been determined by a medical doctor or other specialist who, in consultation with the patient, has determined that the imaging scan is advisable. The protocol 402 at least defines the imaging scan to be implemented to generate acquired imaging data. For example, the protocol 402 may define the area(s) of the patient's body to image and the type of imaging scan to perform. In the exemplary embodiment of a medical CT imaging system 100 described above, the protocol 402 will determine the movement of the object support couch 106, and of the x-ray source 110 and x-ray data measurement system 112, and the x-ray dosage to apply during an imaging scan. The technologist may often implement any one or more of several wholly or partially predefined imaging acquisition protocols 402. In nuclear medicine imaging, implementing the imaging acquisition protocol 402 may involve either asking the imaged patient to ingest a radiopharmaceutical, or injecting the radiopharmaceutical into the bloodstream of the patient.

In addition to the imaging scan to be used to generate acquired imaging data, the imaging acquisition protocol 402 may optionally further include an image reconstruction process. Depending on the imaging modality being utilized, the acquired imaging data recorded directly by the imaging equipment may or may not be the exact data of interest. In some cases, that acquired imaging data may have to be processed using any one of many well-known "reconstruction" processes to generate reconstructed image data for use by medical professionals and the like. As one example, the x-ray transmission data acquired by the medical CT imaging system 100 typically needs to be reconstructed to generate medically useful data. Thus, in such situations, the protocol 402 may include the reconstruction process which will be used to derive reconstructed imaging data from the acquired imaging data. Alternatively, the protocol 402 may not include any such reconstruction processes, leaving the post-acquisition reconstruction data processing to be performed at a later time.

In the next step of the method, the imaging data is acquired 404. That is, the imaged subject is properly situated within the imaging apparatus and an imaging scan is performed to record acquired imaging data according to the protocol 402. In the event the protocol 402 includes an imaging reconstruction process, the step 404 additionally includes the reconstruction to generate reconstructed imaging data from the acquired imaging data.

During the acquisition of imaging data 404, the technologist or an assistant enters identification information 406 into the imaging apparatus. The identification information may be entered manually, automatically, or by a combination of manual and automatic entry. In a manual data entry, the technologist uses a keyboard or other input device to enter identification information into the system from paper records, from interviewing the imaged subject, or from other non-electronic sources. In an automatic data entry, the system obtains the identification information from another electronic database such as radiology information system (RIS) or a hospital information system (HIS). For example, in the medical CT imaging system 100 described above, the technologist may use the user input 124 to manually enter identification information and/or cause the processor 118 to automatically obtain identification information from another electronic database.

At least some of the identification information is entered into the imaging acquisition system during the imaging data acquisition 404. In various embodiments, however, some of the identification information may also be entered either before or after the imaging data acquisition 404. Thus, as one example, some identification information may be entered into the imaging acquisition system before the imaging data acquisition 404, with the remainder being entered during the imaging data acquisition 404. Or, as another example, entry of the identification information may begin after the start of the imaging data acquisition 404, and then continue until entry is completed after the imaging data acquisition 404 is finished. As yet a third example, the identification information may be entered solely during the imaging data acquisition 404. As the identification information is entered during the imaging data acquisition 404, the system associates the information with the acquisition 404 in progress.

In some embodiments, the identification information may also be checked for errors 408 during or after the imaging data acquisition 404. That is, the accuracy and completeness of the entered identification information may be checked against either the original source of information (whether manual or automatic) or against one or more secondary sources of information. If an error is found, it may then be corrected by the technologist.

Once the imaging data acquisition 404 is complete, all the identification information 406 has been entered, and any optional error checking is performed 408, the acquired and/or reconstructed imaging data is then stored along with the entered identification information 410. In one embodiment, the imaging data and identification information is stored in a digital format. This may be accomplished, for example, by creating a file which complies with the DICOM file format 300 discussed above. In that example, the imaging data is stored in the imaging data portion 312 and the entered identification information is stored in the header portion 314. Other formats may of course be used to store 410 the imaging data along with the entered identification information.

In many cases, the technologist will additionally transfer 412 the imaging data along with the entered identification information to be stored at another archiving location which is physically remote from the imaging acquisition system. The archiving location may for example be in another room of a medical facility, or in another building of the medical facility, or in another city entirely.

The invention has been described with reference to the several embodiments. Obviously, modifications and alterations will occur to others upon reading and understanding the preceding detailed description. It is intended that the invention be construed as including all such modifications and alterations insofar as they come within the scope of the appended claims or the equivalents thereof. The invention may take form in various compositions, components and arrangements, combinations and sub-combinations of the elements of the disclosed embodiments.

Having thus described the several embodiments, the invention is now claimed to be:

1. A method for acquiring imaging data and identification information relating to the imaging data using an imaging system, the method comprising:
   implementing an imaging acquisition protocol;
   acquiring imaging data according to the imaging acquisition protocol, wherein an image processor of the imaging system receives and reconstructs the imaging data;
   entering the identification information while acquiring imaging data using the imaging system, wherein the identification information entered during the imaging acquisition comprises at least one of a patient name and a patient identification number, and wherein at least some of the entered identification information is obtained from a data management system; and
   storing the imaging data together with the entered identification information.

2. The method of claim 1, wherein the identification information is entered solely while acquiring imaging data.

3. The method of claim 1, wherein the entry of the identification information begins after a start of acquiring imaging data.

4. The method of claim 1, wherein a first portion of the identification information is entered before a start of acquiring imaging data, and a second portion of the identification information is entered while acquiring imaging data.

5. The method of claim 4, wherein a third portion of the identification information is entered after an end of acquiring imaging data.

6. The method of claim 1, wherein the imaging data is digital imaging data.

7. The method of claim 1, wherein the storing of the imaging data together with the entered identification information comprises storing the imaging data in a first portion of a file and storing the entered identification information in a second portion of the file.

8. The method of claim 7, wherein the storing of the imaging data together with the identification information complies with the DICOM standard.

9. The method of claim 1, further comprising checking the entered identification information for errors while acquiring imaging data.

10. The method of claim 9, further comprising correcting one or more data entry errors before transferring the imaging data and the identification information to a data archive for storage.

11. The method of claim 1, wherein the imaging acquisition protocol reconstructs the imaging data before storing the imaging data.

12. A system for acquiring imaging data and identification information relating to the imaging data, the system comprising a computer, a display operatively connected to the computer, an image processor, and software embodied on a tangible medium and readable by the computer, the software comprising logic to:
  implement an imaging acquisition protocol;
  acquire imaging data according to the imaging acquisition protocol, wherein the image processor of the imaging system receives and reconstructs the imaging data;
  receive the identification information while acquiring imaging data using the imaging system, wherein the identification information received while acquiring imaging data comprises at least one of a patient name and a patient identification number;
  obtain at least some of the received identification information from a data management system; and
  store the imaging data together with the received identification information.

13. The system of claim 12, wherein the receipt of the identification information begins after a start of acquiring imaging data.

14. The system of claim 12, wherein the imaging data is digital imaging data.

15. The system of claim 12, wherein the storing of the imaging data together with the received identification information comprises storing the imaging data in a first portion of a file and storing the entered identification information in a second portion of the file.

16. The system of claim 15, wherein the storing of the imaging data together with the identification information complies with the DICOM standard.

17. The system of claim 12, wherein the software further comprises logic to check the received identification information for errors while acquiring imaging data.

18. The system of claim 12, wherein the software further comprises logic to reconstruct the imaging data before storing the imaging data.

19. A method for acquiring digital imaging data and identification information relating to the imaging data using an imaging system, the method comprising:
  implementing an imaging acquisition protocol;
  acquiring imaging data according to the imaging acquisition protocol, wherein an image processor of the Imaging system receives and reconstructs the imaging data;
  entering at least some of the identification information while acquiring imaging data using the imaging system,
  wherein the identification information received while acquiring imaging data comprises at least one of a patient name and a patient identification number;
  checking the entered identification information for errors while acquiring imaging data; and
  storing the imaging data together with the entered identification information.

* * * * *